United States Patent
Bogdan et al.

(10) Patent No.: US 6,686,326 B2
(45) Date of Patent: Feb. 3, 2004

(54) AZEOTROPE-LIKE COMPOSITIONS OR PENTAFLUOROBUTANE

(75) Inventors: Mary C. Bogdan, Buffalo, NY (US); Kane D. Cook, Eggertsville, NY (US); Hang T. Pham, Amherst, NY (US); Gary M. Knopeck, Lakeview, NY (US); Rajiv R. Singh, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 43 days.

(21) Appl. No.: 10/161,361

(22) Filed: Jun. 3, 2002

(65) Prior Publication Data
US 2003/0022802 A1 Jan. 30, 2003

Related U.S. Application Data

(60) Provisional application No. 60/295,053, filed on Jun. 1, 2001.

(51) Int. Cl.[7] .............................. C08J 9/14; B29C 44/24
(52) U.S. Cl. ................. 510/411; 510/177; 510/273; 510/365; 510/407; 510/410; 510/417
(58) Field of Search ................. 510/411, 410, 510/177, 273, 417, 407, 409, 365, 178; 521/130, 131

(56) References Cited

U.S. PATENT DOCUMENTS

| | | | |
|---|---|---|---|
| 2,834,748 A | 5/1958 | Bailey et al. | 260/42 |
| 2,846,458 A | 8/1958 | Haluska | 260/448.2 |
| 2,917,480 A | 12/1959 | Bailey et al. | 260/42 |
| 3,966,726 A | 6/1976 | Toth et al. | |
| 4,975,156 A | 12/1990 | Wismer | |
| 5,268,120 A | 12/1993 | Michaud | |
| 5,268,121 A | 12/1993 | Michaud | |
| 6,365,566 B1 * | 4/2002 | Bogdan et al. | |

* cited by examiner

Primary Examiner—Gregory E. Webb
(74) Attorney, Agent, or Firm—Colleen D. Szuch

(57) ABSTRACT

Disclosed are azeotrope-like compositions comprising 1,1,1,3,3-pentafluorobutane, water and a hydrocarbon selected from the group consisting of n-pentane, isopentane, cyclopentane, n-hexane, and isohexane., said compositions are environmentally desirable for use as refrigerants, aerosol propellants, metered dose inhalers, blowing agents for polymer foam, heat transfer media, and gaseous dielectrics.

25 Claims, 1 Drawing Sheet

Ternary Plot of Boiling Points
Iso Hexane, boiling pt. 60.2 C
Water (H2O) boiling Pt. 100 C
HFC-365mfc, boiling pt. 40.4 C
—●— boiling point along this line is lower than any of the three components

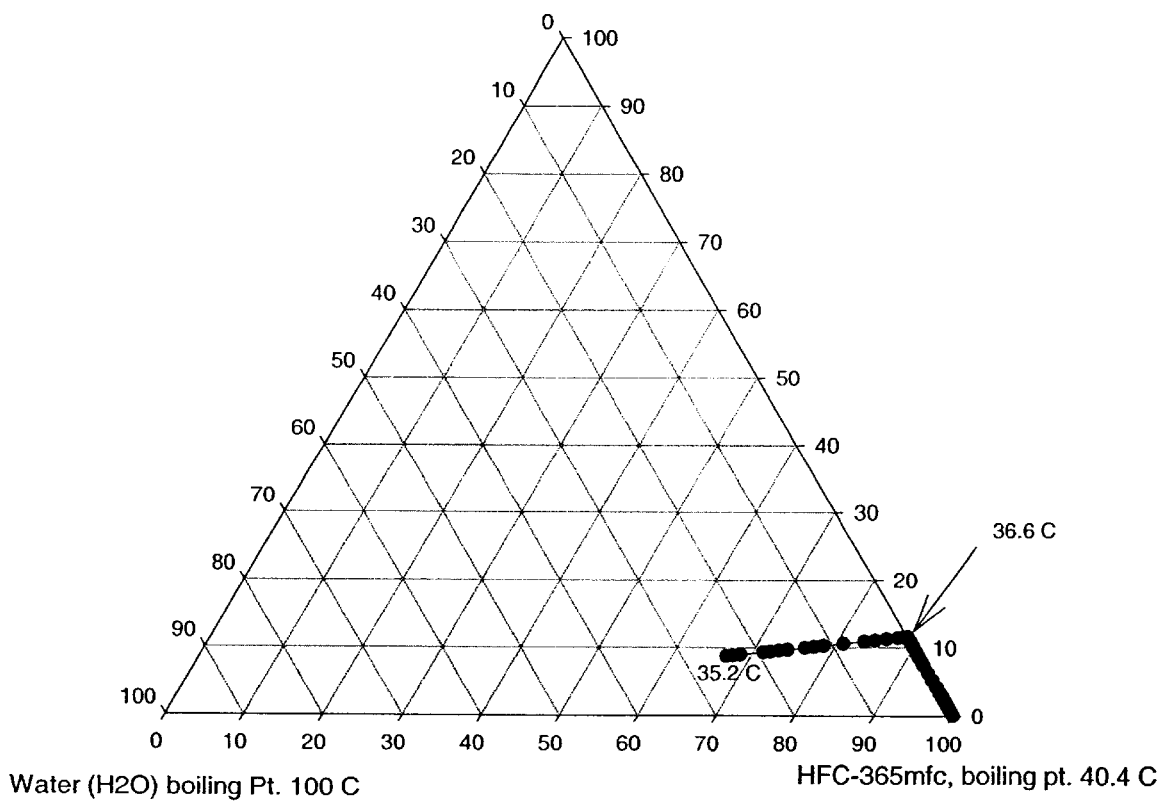

AZEOTROPE-LIKE COMPOSITIONS OR PENTAFLUOROBUTANE

CROSS-REFERENCE TO RELATED APPLICATION

This application claims priority to provisional application serial No. 60/295,053, which was filed with the United States Patent and Trademark Office on Jun. 1, 2001, and is incorporated herein by reference.

FIELD OF THE INVENTION

The present invention relates to novel compositions comprising fluorocarbons, hydrocarbons and water.

BACKGROUND

Fluorocarbon based fluids have found widespread use in industry in a number of applications, including as refrigerants, aerosol propellants, blowing agents, heat transfer media, and gaseous dielectrics. Because of the suspected environmental problems associated with the use of some of these fluids, it is desirable to use fluids having low or even zero ozone depletion potential, such as hydrofluorocarbons ("HFC's").

Thus, the use of fluids that do not contain chlorofluorocarbons ("CFCs") or hydrochlorofluorocarbons ("HCFCs") is desirable. Additionally, it is known that the use of single component fluids or azeotropic mixtures, which mixtures do not fractionate on boiling and evaporation, is desirable. However, the identification of new, environmentally safe, non-fractionating mixtures is complicated due to the fact that azeotrope formation is not readily predictable.

The art continually is seeking new fluorocarbon based mixtures that offer alternatives to, and are considered environmentally safer substitutes for, CFC's and HCFCs. Of particular interest are combinations or mixtures containing a fluorocarbon and a non-fluorocarbon, both of low or no ozone depletion potentials. Such mixtures are the subject of this invention. As used herein, the term fluorocarbon includes CFCs and HCFCs.

BRIEF DESCRIPTION OF THE DRAWING

FIG. 1 is a plot of the boiling point curve for ternary mixtures comprising HFC-365mfc, isohexane and water.

DETAILED DESCRIPTION OF THE INVENTION AND PREFERRED EMBODIMENTS

The present inventors have developed several compositions that can help to satisfy the continuing need for substitutes for CFCs and HCFCs. In one embodiment, the present invention provides azeotrope-like compositions comprising pentafluorobutane, water and a hydrocarbon selected from the group consisting of n-pentane, isopentane, cyclopentane, n-hexane, and isohexane.

The preferred compositions of the invention provide environmentally desirable, zero ozone depletion potential replacements for currently used CFC's and HCFC's. Additionally, the compositions of the invention exhibit characteristics that make the compositions better CFC and HCFC substitutes than any of HFC-365mfc, n-pentane, isopentane, cyclopentane, n-hexane, isohexane or water alone.

Compositions

The present compositions are azeotrope-like compositions. As used herein, the term "azeotrope-like" is intended in its broad sense to include both compositions that are strictly azeotropic and compositions that behave like azeotropic mixtures. From fundamental principles, the thermodynamic state of a fluid is defined by pressure, temperature, liquid composition, and vapor composition. An azeotropic mixture is a system of two or more components in which the liquid composition and vapor composition are equal at a given pressure and temperature. In practice, this means that the components of an azeotropic mixture are constant boiling and cannot be separated during a phase change.

Azeotrope-like compositions are constant boiling or essentially constant boiling. In other words, for azeotrope-like compositions, the composition of the vapor formed during boiling or evaporation is identical, or substantially identical, to the original liquid composition. Thus, with boiling or evaporation, the liquid composition changes, if at all, only to a minimal or negligible extent. This is to be contrasted with non-azeotrope-like compositions in which, during boiling or evaporation, the liquid composition changes to a substantial degree. All azeotrope-like compositions of the invention within the indicated ranges as well as certain compositions outside these ranges are azeotrope-like.

The azeotrope-like compositions of the invention may include additional components that do not form new azeotropic or azeotrope-like systems, or additional components that are not in the first distillation cut. The first distillation cut is the first cut taken after the distillation column displays steady state operation under total reflux conditions. One way to determine whether the addition of a component forms a new azeotropic or azeotrope-like system so as to be outside of this invention is to distill a sample of the composition with the component under conditions that would be expected to separate a non-azeotropic mixture into its separate components. If the mixture containing the additional component is non-azeotropic or non-azeotrope-like, the additional component will fractionate from the azeotropic or azeotrope-like components. If the mixture is azeotrope-like, some finite amount of a first distillation cut will be obtained that contains all of the mixture components that is constant boiling or behaves as a single substance.

It follows from this that another characteristic of azeotrope-like compositions is that there is a range of compositions containing the same components in varying proportions that are azeotrope-like or constant boiling. All such compositions are intended to be covered by the terms "azeotrope-like" and "constant boiling". As an example, it is well known that at differing pressures, the composition of a given azeotrope will vary at least slightly, as does the boiling point of the composition. Thus, an azeotrope of A and B represents a unique type of relationship, but with a variable composition depending on temperature and/or pressure. It follows that, for azeotrope-like compositions, there is a range of compositions containing the same components in varying proportions that are azeotrope-like. All such compositions are intended to be covered by the term azeotrope-like as used herein.

Pentafluorobutane/n-pentane/Water

One embodiment of the present invention provides azeotrope-like compositions comprising HFC-365mfc, n-pentane and water. Preferably, the novel azeotrope-like compositions of the present invention comprise effective amounts of HFC-365mfc, n-pentane and water. The term "effective amounts" as used herein refers to the amount of each component which upon combination with the other component or components, results in the formation of the present azeotrope-like compositions.

These embodiments preferably provide azeotrope-like compositions comprising, and preferably consisting essentially of, from about 10 to about 98 parts by weight HFC-365mfc, from about 1 to about 80 parts by weight of n-pentane, and from about 1 to about 80 parts by weight of water. Such compositions are characterized by a boiling point of about 36° C.±4° C., preferably ±2° C., more preferably ±1° C. at about 760 mmHg.

The preferred, more preferred, and most preferred compositions of this embodiment are set forth in Table 1. The numerical ranges in Table 1 are to be understood to be prefaced by the term "about".

TABLE 1

| Components | Preferred (wt %) | More Preferred (wt %) | Most Preferred (wt %) |
|---|---|---|---|
| HFC-365mfc | 10–98 | 40–98 | 60–98 |
| n-pentane | 80–1 | 40–1 | 30–1 |
| water | 80–1 | 40–1 | 30–1 |

Pentafluorobutane/Isopentane/Water

One embodiment of the present invention provides azeotrope-like compositions comprising HFC-365mfc, isopentane and water. Preferably, the novel azeotrope-like compositions of the present invention comprise effective amounts of HFC-365mfc, isopentane and water.

These embodiments preferably provide azeotrope-like compositions comprising, and preferably consisting essentially of, from about 10 to about 98 parts by weight HFC-365mfc, from about 1 to about 80 parts by weight of isopentane, and from about 1 to about 80 parts by weight of water. Such compositions are characterized by a boiling point of about 36° C.±4° C., preferably ±2° C., more preferably ±1° C. at about 760 mmHg.

The preferred, more preferred, and most preferred compositions of this embodiment are set forth in Table 2. The numerical ranges in Table 2 are to be understood to be prefaced by the term "about".

TABLE 2

| Components | Preferred (wt %) | More Preferred (wt %) | Most Preferred (wt %) |
|---|---|---|---|
| HFC-365mfc | 10–98 | 40–98 | 60–98 |
| isopentane | 80–1 | 40–1 | 30–1 |
| water | 80–1 | 40–1 | 30–1 |

Pentafluorobutane/Cyclopentane/Water

One embodiment of the present invention provides azeotrope-like compositions comprising HFC-365mfc, cyclopentane and water. Preferably, the novel azeotrope-like compositions of the present invention comprise effective amounts of HFC-365mfc, cyclopentane and water.

These embodiments preferably provide azeotrope-like compositions comprising, and preferably consisting essentially of, from about 10 to about 98 parts by weight HFC-365mfc, from about 1 to about 80 parts by weight of cyclopentane, and from about 1 to about 80 parts by weight of water. Such compositions are characterized by a boiling point of about 36° C.±4° C., preferably ±2° C., more preferably ±1° C. at about 760 mmHg.

The preferred, more preferred, and most preferred compositions of this embodiment are set forth in Table 3. The numerical ranges in Table 3 are to be understood to be prefaced by the term "about".

TABLE 3

| Components | Preferred (wt %) | More Preferred (wt %) | Most Preferred (wt %) |
|---|---|---|---|
| HFC-365mfc | 10–98 | 40–98 | 60–98 |
| cyclopentane | 80–1 | 40–1 | 30–1 |
| water | 80–1 | 40–1 | 30–1 |

Pentafluorobutane/n-hexane/Water

One embodiment of the present invention provides azeotrope-like compositions comprising HFC-365mfc, n-hexane and water. Preferably, the novel azeotrope-like compositions of the present invention comprise effective amounts of HFC-365mfc, n-hexane and water.

These embodiments preferably provide azeotrope-like compositions comprising, and preferably consisting essentially of, from about 10 to about 98 parts by weight HFC-365mfc, from about 1 to about 80 parts by weight of n-hexane, and from about 1 to about 80 parts by weight of water. Such compositions are characterized by a boiling point of about 36° C.±4° C., preferably ±2° C., more preferably ±1° C. at about 760 mmHg.

The preferred, more preferred, and most preferred compositions of this embodiment are set forth in Table 4. The numerical ranges in Table 4 are to be understood to be prefaced by the term "about".

TABLE 4

| Components | Preferred (wt %) | More Preferred (wt %) | Most Preferred (wt %) |
|---|---|---|---|
| HFC-365mfc | 10–98 | 40–98 | 60–98 |
| n-hexane | 80–1 | 40–1 | 30–1 |
| water | 80–1 | 40–1 | 30–1 |

Pentafluorobutane/Isohexane/Water

One embodiment of the present invention provides azeotrope-like compositions comprising HFC-365mfc, isohexane and water. Preferably, the novel azeotrope-like compositions of the present invention comprise effective amounts of HFC-365mfc, isohexane and water.

These embodiments preferably provide azeotrope-like compositions comprising, and preferably consisting essentially of, from about 10 to about 98 parts by weight HFC-365mfc, from about 1 to about 80 parts by weight of isohexane, and from about 1 to about 80 parts by weight of water. Such compositions are characterized by a boiling point of about 36° C. ±4° C., preferably ±2° C., more preferably ±1° C. at about 760 mmHg.

The preferred, more preferred, and most preferred compositions of this embodiment are set forth in Table 5. The numerical ranges in Table 5 are to be understood to be prefaced by the term "about".

TABLE 5

| Components | Preferred (wt %) | More Preferred (wt %) | Most Preferred (wt %) |
|---|---|---|---|
| HFC-365mfc | 10–98 | 40–98 | 60–98 |
| isohexane | 80–1 | 40–1 | 30–1 |
| water | 80–1 | 40–1 | 30–1 |

The boiling point curve for this embodiment of the invention is illustrated in FIG. 1. Table 6 provides boiling point data for the HFC-365mfc/isohexane/water compositions according to preferred embodiments of the present invention.

Uses of the Compositions

The compositions of the present invention may be used in a wide variety of applications as substitutes for CFCs and HCFCs. For example, the present compositions are useful as solvents, blowing agents, refrigerants, cleaning agents and aerosols.

One embodiment of the present invention relates to a blowing agent comprising one or more of the azeotrope-like compositions of the invention. In other embodiments, the invention provides foamable compositions, and preferably polyurethane and polyisocyanurate foam compositions, and methods of preparing foams. In such foam embodiments, one or more of the present azeotrope-like compositions are included as a blowing agent in a foamable composition, which composition preferably includes one or more additional components capable of reacting and foaming under the proper conditions to form a foam or cellular structure, as is well known in the art. The present methods preferably comprise providing such a foamable composition and reacting it under conditions effective to obtain a foam, and preferably a closed cell foam. The invention also relates to foam, and preferably closed cell foam, prepared from a polymer foam formulation containing a blowing agent comprising the azeotrope-like composition of the invention.

Any of the methods well known in the art, such as those described in "Polyurethanes Chemistry and Technology," Volumes I and II, Saunders and Frisch, 1962, John Wiley and Sons, New York, N.Y., which is incorporated herein by reference, may be used or adapted for use in accordance with the foam embodiments of the present invention. In general, such preferred methods comprise preparing polyurethane or polyisocyanurate foams by combining an isocyanate, a polyol or mixture of polyols, a blowing agent or mixture of blowing agents comprising one or more of the present compositions, and other materials such as catalysts, surfactants, and optionally, flame retardants, colorants, or other additives. It is convenient in many applications to provide the components for polyurethane or polyisocyanurate foams in pre-blended formulations. Most typically, the foam formulation is pre-blended into two components. The isocyanate and optionally certain surfactants and blowing agents comprise the first component, commonly referred to as the "A" component. The polyol or polyol mixture, surfactant, catalysts, blowing agents, flame retardant, and other isocyanate reactive components comprise the second component, commonly referred to as the "B" component. Accordingly, polyurethane or polyisocyanurate foams are readily prepared by bringing together the A and B side components either by hand mix for small preparations and, preferably, machine mix techniques to form blocks, slabs, laminates, pour-in-place panels and other items, spray applied foams, froths, and the like. Optionally, other ingredients such as fire retardants, colorants, auxiliary blowing agents, and even other polyols can be added as a third stream to the mix head or reaction site. Most conveniently, however, they are all incorporated into one B-component as described above.

It is also possible to produce thermoplastic foams using the compositions of the invention. For example, conventional foam polyurethanes and isocyanurate formulations may be combined with the azeotrope-like compositions in a conventional manner to produce rigid foams.

Azeotrope-like mixtures containing HFC-365mfc in accordance with the present invention are particularly suitable as foam blowing agents since foams blown with HFC-365mfc have been found to possess low relative initial and aged thermal conductivity and good dimensional stability at low temperatures. Of particular interest are those azeotrope-like compositions of the present invention that optionally further contain other zero ozone depleting materials, such as, for example, other hydrofluorocarbons, e.g., difluoromethane (HFC-32); difluoroethane (HFC-152); trifluoroethane (HFC-143); tetrafluoroethane (HFC-134); pentafluoroethane (HFC-125); pentafluoropropane (HFC-245); hexafluoropropane (HFC-236); heptafluoropropane (HFC-227); and inert gases, e.g., air, nitrogen, carbon dioxide. Where isomerism is possible for the hydrofluorocarbons mentioned above, the respective isomers may be used either singly or in the form of a mixture.

Dispersing agents, cell stabilizers, and surfactants may also be incorporated into the blowing agent mixture. Surfactants, better known as silicone oils, are added to serve as cell stabilizers. Some representative materials are sold under the names of DC-193, B-8404, and L-5340 which are, generally, polysiloxane polyoxyalkylene block co-polymers such as those disclosed in U.S. Pat. Nos. 2,834,748, 2,917, 480, and 2,846,458. Other optional additives for the blowing agent mixture may include flame retardants such as tri(2-chloroethyl)phosphate, tri(2-chloropropyl)phosphate, tri(2,3-dibromopropyl)-phosphate, tri(1,3-dichloropropyl) phosphate, diammonium phosphate, various halogenated aromatic compounds, antimony oxide, aluminum trihydrate, polyvinyl chloride, and the like.

In another embodiment, the azeotrope-like compositions of this invention may be used as propellants in sprayable compositions, either alone or in combination with known propellants. The sprayable composition comprises, consists essentially of, and consists of a material to be sprayed and a propellant comprising, consisting essentially of, and consisting of the azeotrope-like compositions of the invention. Inert ingredients, solvents, and other materials may also be present in the sprayable mixture. Preferably, the sprayable composition is an aerosol. Suitable materials to be sprayed include, without limitation, cosmetic materials such as deodorants, perfumes, hair sprays, cleansers, and polishing agents as well as medicinal materials such as anti-asthma and anti-halitosis medications.

In another process embodiment, a process for removing water from HFC-365mfc is provided, which process comprises the step of distilling a mixture of HFC-365, water and a hydrofluorocarbon selected from the group consisting of n-pentane, isopentane, cyclopentane, n-hexane, and isohexane to separate an azeotrope-like composition consisting essentially of HFC-365, the hydrofluorocarbon of the azeotrope-like composition and water. Thus, an azeotrope-like mixture of HFC-365, water and a hydrofluorocarbon selected from the group consisting of n-pentane, isopentane, cyclopentane, n-hexane, and isohexane azeotrope can be used to remove bulk amounts of water in a HFC-365mfc manufacturing process. In another embodiment of the invention, a process is provided in which a mixture of HFC-365, water and a hydrofluorocarbon selected from the group consisting of n-pentane, isopentane, cyclopentane, n-hexane, and isohexane is phase separated to remove bulk amounts of water before conducting said distillation step. Residual amounts of water in the HFC-365mfc phase can be distilled out because of the existence of the azeotropes. Subsequent distillation or multiple distillations can be used to remove trace amounts of water along with other impurities to achieve the desired purity.

The components of the composition of the invention are known materials that are commercially available or may be prepared by known methods. Preferably, the components are of sufficiently high purity so as to avoid the introduction of adverse influences upon cooling or heating properties, constant boiling properties, or blowing agent properties of the system. In the case of metered dose inhalers, the relevant current Good Manufacturing Process may be used for manufacturing these materials.

Additional components may be added to tailor the properties of the azeotrope-like compositions of the invention as needed. By way of example, oil solubility aids may be added in the case in which the compositions of the invention are used as refrigerants. Stabilizers and other materials may also be added to enhance the properties of the compositions of the invention.

EXAMPLES

The present invention will be further understood in light of the following examples which are illustrative, but not intended to be limiting.

Example 1

An ebulliometer consisting of vacuum jacketed tube with a condenser on top was used. About 20 g HFC-365mfc were charged to the ebulliometer and then isohexane was added in small, measured increments and water was added in small, measured increments. Temperature depression was observed when isohexane and water were added to HFC-365mfc, indicating a ternary minimum boiling azeotrope is formed. From about 0.1 to about 30-weight percent isohexane, and from about 0.1 to about 30 weight percent of water, the boiling point of the composition changed by about 3° C. or less. The ternary mixtures shown in Table 6 were studied and the boiling point of the compositions changed by about 3° C. Therefore, the composition exhibits azeotrope and/or azeotrope-like properties over this range. FIG. 1 is a graphical representation of the boiling point data of Table 6.

TABLE 6

| Barometer = 14.55 psia | | | |
|---|---|---|---|
| Wt. % 365mfc | Wt. % I-hexane | Wt. % water | T (C.) |
| 100.00 | 0.00 | 0.00 | 40.44 |
| 99.85 | 0.15 | 0.00 | 40.37 |
| 99.55 | 0.45 | 0.00 | 40.14 |
| 99.25 | 0.75 | 0.00 | 40.05 |
| 98.96 | 1.04 | 0.00 | 39.84 |
| 98.37 | 1.63 | 0.00 | 39.44 |
| 97.79 | 2.21 | 0.00 | 39.13 |
| 97.22 | 2.78 | 0.00 | 38.83 |
| 96.65 | 3.35 | 0.00 | 38.42 |
| 95.82 | 4.18 | 0.00 | 38.02 |
| 94.72 | 5.28 | 0.00 | 37.71 |
| 93.66 | 6.34 | 0.00 | 36.85 |
| 92.61 | 7.39 | 0.00 | 36.90 |
| 92.10 | 7.90 | 0.00 | 36.75 |
| 91.34 | 8.66 | 0.00 | 36.70 |
| 90.59 | 9.41 | 0.00 | 36.63 |
| 89.86 | 10.14 | 0.00 | 36.45 |
| 89.13 | 10.87 | 0.00 | 36.55 |
| 88.42 | 11.58 | 0.00 | 36.60 |
| 88.06 | 11.53 | 0.41 | 36.34 |
| 87.35 | 11.44 | 1.21 | 36.09 |
| 85.97 | 11.26 | 2.77 | 36.04 |
| 84.63 | 11.08 | 4.29 | 35.63 |
| 83.33 | 10.91 | 5.76 | 35.51 |
| 82.07 | 10.75 | 7.19 | 35.48 |
| 80.84 | 10.59 | 8.57 | 35.43 |
| 79.65 | 10.43 | 9.91 | 35.33 |
| 78.50 | 10.28 | 11.22 | 35.28 |
| 77.38 | 10.13 | 12.49 | 35.28 |
| 76.29 | 9.99 | 13.72 | 35.28 |
| 75.23 | 9.85 | 14.91 | 35.28 |

TABLE 6-continued

| Barometer = 14.55 psia | | | |
|---|---|---|---|
| Wt. % 365mfc | Wt. % I-hexane | Wt. % water | T (C.) |
| 74.20 | 9.72 | 16.08 | 35.28 |
| 73.20 | 9.59 | 17.21 | 35.18 |
| 72.23 | 9.46 | 18.31 | 35.18 |
| 71.28 | 9.33 | 19.39 | 35.18 |
| 70.35 | 9.21 | 20.43 | 35.18 |
| 69.45 | 9.09 | 21.45 | 35.18 |
| 68.57 | 8.98 | 22.45 | 35.18 |
| 67.72 | 8.87 | 23.41 | 35.18 |
| 66.88 | 8.76 | 24.36 | 35.18 |

Example 2

An ebulliometer consisting of vacuum jacketed tube with a condenser on top was used. About 20 g HFC-365mfc were charged to the ebulliometer and then n-pentane was added in small, measured increments and water was added in small, measured increments. Temperature depression was observed when n-pentane and water were added to HFC-365mfc, indicating a ternary minimum boiling azeotrope is formed. From about 0.1 to about 30-weight percent n-pentane, and from about 0.1 to about 30 weight percent of water, the boiling point of the composition changed by about 3° C. or less. Therefore, the composition exhibits azeotrope and/or azeotrope-like properties over this range.

Example 3

An ebulliometer consisting of vacuum jacketed tube with a condenser on top was used. About 20 g HFC-365mfc were charged to the ebulliometer and then cyclopentane was added in small, measured increments and water was added in small, measured increments. Temperature depression was observed when cyclopentane and water were added to HFC-365mfc, indicating a ternary minimum boiling azeotrope is formed. From about 0.1 to about 30-weight percent cyclopentane, and from about 0.1 to about 30 weight percent of water, the boiling point of the composition changed by about 3° C. or less. Therefore, the composition exhibits azeotrope and/or azeotrope-like properties over this range.

Example 4

An ebulliometer consisting of vacuum jacketed tube with a condenser on top was used. About 20 g HFC-365mfc were charged to the ebulliometer and then n-hexane was added in small, measured increments and water was added in small, measured increments. Temperature depression was observed when n-hexane and water were added to HFC-365mfc, indicating a ternary minimum boiling azeotrope is formed. From about 0.1 to about 30-weight percent n-hexane, and from about 0.1 to about 30 weight percent of water, the boiling point of the composition changed by about 3° C. or less. Therefore, the composition exhibits azeotrope and/or azeotrope-like properties over this range.

Example 5

An ebulliometer consisting of vacuum jacketed tube with a condenser on top was used. About 20 g HFC-365mfc were charged to the ebulliometer and then isopentane was added in small, measured increments and water was added in small, measured increments. Temperature depression was observed when isopentane and water were added to HFC-365mfc, indicating a ternary minimum boiling azeotrope is formed. From about 0.1 to about 30-weight percent isopentane, and from about 0.1 to about 30 weight percent of water, the boiling point of the composition changed by about 3° C. or less. Therefore, the composition exhibits azeotrope and/or azeotrope-like properties over this range.

Example 6

This example illustrates the thermal data associated with foams prepared using blowing agent compositions according to the present invention.

The following materials are used in Example 6 and Comparative Example 1.

Polyol: A polyester polyol with an OH number of 240. It is a commercially available material from Stepan.

Isopentane: 2-methylbutane commercially available from Phillips 66 Company as Borger Isopentane HFC-365mfc: 1,1,1,3,3-pentafluorobutane available from Solvay.

Surfactant A: A polysiloxane polyether copolymer, which is commercially available from Goldschmidt.

Catalyst A: An inorganic potassium based amine, which is commercially available from Air Products.

Catalyst B: A commercially available trimerization catalyst, which is commercially available from Air Products Two foams ("Job #00-26-1" and "Job #00-26-2") are prepared by a general procedure commonly referred to as "handmixing". For each blowing agent or blowing agent pair, a premix of polyol, surfactant, and catalysts is prepared in the same proportions displayed in Table 7. About 100 grams of each formulation is blended. The premix is blended in a 32 oz paint can, and stirred at about 1500 rpm with a Conn 2" diameter ITC mixer until a homogeneous blend is achieved.

When mixing is complete, the can is covered and placed in a refrigerator controlled at 50° F. The foam blowing agent or pre-blended pair of blowing agents is also stored in pressure bottles at 50° F. The A component is kept in sealed containers at 70° F.

The pre-cooled blowing agent is added in the required amount to the premix. The contents are stirred for two minutes with a Conn 2" ITC mixing blade turning at 1000 rpm. Following this, the mixing vessel and contents are re-weighed. If there is a weight loss, the blowing agent or the blend is added to the solution to make up any weight loss. The can is then covered and replaced in the refrigerator.

After the contents have cooled again to 50° F., approximately 10 minutes, the mixing vessel is removed from refrigerator and taken to the mixing station. A pre-weighted portion of A-component, isocyanurate, is added quickly to the B-component, the ingredients are mixed for 10 seconds using a Conn 2" diameter ITC mixing blade at 3000 rpm and poured into a 8"×8"×4" cardboard cake box and allowed to rise. Cream, initiation, gel and tack free times are recorded for the individual polyurethane foam samples.

The foams are allowed to cure in the boxes at room temperature for at least 24 hours. After curing, the blocks are trimmed to a uniform size and densities measured.

The foams are tested for k-factor according to ASTM C518 using a mean temperature of 36.5° F. The k-factor results are listed in Table 7.

TABLE 7

| Job # | 00-26-1 | 00-26-2 |
|---|---|---|
| Component (pbw) | | |
| Polyol | 100 | 100 |
| Surfactant | 2 | 2 |
| Catalyst A | 0.5 | 0.63 |
| Catalyst B | 3.8 | 5.6 |
| Water | 1.7 | 2.8 |
| HFC-365mfc | 12.8 | 10.3 |
| Isopentane | 6.2 | 5 |
| Index | 250 | 250 |
| Density | 2.05 | 2.05 |
| Process Temp (iso/polyol) (° F.) | 70/50 | 70/50 |
| k-factor 36.5° F. | 0.147 | 0.172 |

Comparative Example 1

Three foams ("Job #00-25-1", "Job #00-25-2" and "Job #00-25-3") are prepared using HFC-365 and water, but no isopentane, as blowing agents, and the resulting k-factors are measured as in Example 6. For each blowing agent or blowing agent pair, a premix of polyol, surfactant, and catalysts is prepared in the same proportions displayed in Table 8.

TABLE 8

| Job # | 00-25-1 | 00-25-2 | 00-25-3 |
|---|---|---|---|
| Component (pbw) | | | |
| Polyol | 100 | 100 | 100 |
| Surfactant | 2 | 2 | 2 |
| Catalyst A | 0.25 | 0.5 | 0.63 |
| Catalyst B | 2.8 | 3.8 | 5.6 |
| Water | 0 | 1.7 | 2.8 |
| HFC-365mfc | 38 | 25.5 | 20.5 |
| Isopentane | 0 | 0 | 0 |
| Index | 250 | 250 | 250 |
| Density | 1.98 | 2.05 | 2.04 |
| Process Temp (iso/polyol) (° F.) | 70/50 | 70/50 | 70/50 |
| k-factor 36.5° F. | 0.16 | 0.15 | 0.227 |

As shown in the table, the k-factors of foams blown with HFC-365mfc and water exhibit k-factors that are worse (higher) than the k-factors of foams blown with comparable HFC-365/isopentane/water blowing agents.

What is claimed is:

1. An azeotrope-like composition comprising 1,1,1,3,3-pentafluorobutane, water, and a hydrocarbon selected from the group consisting of n-pentane, isopentane, cyclopentane, n-hexane, and isohexane.

2. The azeotrope-like composition of claim 1 characterized by a constant boiling point of from about 36° C.±4° C. at about 760 mmHg.

3. The azeotrope-like composition of claim 1 consisting essentially of from about 10 to about 98 parts by weight HFC-365mfc, from about 1 to about 80 parts by weight of n-pentane, and from about 1 to about 80 parts by weight of water.

4. The azeotrope-like composition of claim 3 consisting essentially of from about 40 to about 98 parts by weight HFC-365mfc, from about 1 to about 40 parts by weight of n-pentane, and from about 1 to about 40 parts by weight of water.

5. The azeotrope-like composition of claim 4 consisting essentially of from about 60 to about 98 parts by weight HFC-365mfc, from about 1 to about 30 parts by weight of n-pentane, and from about 1 to about 30 parts by weight of water.

6. The azeotrope-like composition of claim 1 consisting essentially of from about 10 to about 98 parts by weight HFC-365mfc, from about 1 to about 80 parts by weight of isopentane, and from about 1 to about 80 parts by weight of water.

7. The azeotrope-like composition of claim 6 consisting essentially of from about 40 to about 98 parts by weight HFC-365mfc, from about 1 to about 40 parts by weight of isopentane, and from about 1 to about 40 parts by weight of water.

8. The azeotrope-like composition of claim 7 consisting essentially of from about 60 to about 98 parts by weight HFC-365mfc, from about 1 to about 30 parts by weight of isopentane, and from about 1 to about 30 parts by weight of water.

9. The azeotrope-like composition of claim 1 consisting essentially of from about 10 to about 98 parts by weight HFC-365mfc, from about 1 to about 80 parts by weight of cyclopentane, and from about 1 to about 80 parts by weight of water.

10. The azeotrope-like composition of claim 9 consisting essentially of from about 40 to about 98 parts by weight HFC-365mfc, from about 1 to about 40 parts by weight of cyclopentane, and from about 1 to about 40 parts by weight of water.

11. The azeotrope-like composition of claim 10 consisting essentially of from about 60 to about 98 parts by weight HFC-365mfc, from about 1 to about 30 parts by weight of cyclopentane, and from about 1 to about 30 parts by weight of water.

12. The azeotrope-like composition of claim 1 consisting essentially of from about 10 to about 98 parts by weight HFC-365mfc, from about 1 to about 80 parts by weight of n-hexane, and from about 1 to about 80 parts by weight of water.

13. The azeotrope-like composition of claim 12 consisting essentially of from about 40 to about 98 parts by weight HFC-365mfc, from about 1 to about 40 parts by weight of n-hexane, and from about 1 to about 40 parts by weight of water.

14. The azeotrope-like composition of claim 13 consisting essentially of from about 60 to about 98 parts by weight HFC-365mfc, from about 1 to about 30 parts by weight of n-hexane, and from about 1 to about 30 parts by weight of water.

15. The azeotrope-like composition of claim 1 consisting essentially of from about 10 to about 98 parts by weight HFC-365mfc, from about 1 to about 80 parts by weight of isohexane, and from about 1 to about 80 parts by weight of water.

16. The azeotrope-like composition of claim 15 consisting essentially of from about 40 to about 98 parts by weight HFC-365mfc, from about 1 to about 40 parts by weight of isohexane, and from about 1 to about 40 parts by weight of water.

17. The azeotrope-like composition of claim 16 consisting essentially of from about 60 to about 98 parts by weight HFC-365mfc, from about 1 to about 30 parts by weight of isohexane, and from about 1 to about 30 parts by weight of water.

18. A method for producing a foam comprising foaming a composition containing an azeotrope-like composition of claim 1.

19. A premix of a polyol and a blowing agent comprising a composition of claim 1.

20. A closed cell foam composition prepared by foaming a foamable composition containing an azeotrope-like compositions of claim 1.

21. A blowing agent comprising an azeotrope-like composition of claim 1.

22. A sprayable composition comprising a material to be sprayed and a propellant comprising an azeotrope-like composition of claim 1.

23. The sprayable composition according to claim 22 wherein the sprayable composition is an aerosol.

24. The sprayable composition according to claim 23 wherein the sprayable composition is a cosmetic material.

25. The sprayable composition according to claim 23 wherein the material to be sprayed is a medicinal material.

* * * * *